US010314744B2

(12) United States Patent
Rynerson (10) Patent No.: US 10,314,744 B2
(45) Date of Patent: *Jun. 11, 2019

(54) METHOD AND APPARATUS FOR REDUCING INTRAOCULAR PRESSURE OF AN EYE

(71) Applicant: James M. Rynerson, Franklin, KY (US)

(72) Inventor: James M. Rynerson, Franklin, KY (US)

(*) Notice: Subject to any disclaimer, the term of this patent is extended or adjusted under 35 U.S.C. 154(b) by 87 days.

This patent is subject to a terminal disclaimer.

(21) Appl. No.: 15/651,591

(22) Filed: Jul. 17, 2017

(65) Prior Publication Data

US 2017/0312132 A1 Nov. 2, 2017

Related U.S. Application Data

(63) Continuation of application No. 13/778,209, filed on Feb. 27, 2013, now Pat. No. 9,707,128.

(51) Int. Cl.
*A61F 9/00* (2006.01)
*A61F 9/007* (2006.01)

(52) U.S. Cl.
CPC ................ *A61F 9/00781* (2013.01)

(58) Field of Classification Search
CPC .......................... A61F 9/00781; A61M 27/002
See application file for complete search history.

(56) References Cited

U.S. PATENT DOCUMENTS

| 3,159,161 | A | 12/1964 | Ness |
| 5,338,291 | A | 8/1994 | Speckman et al. |
| 7,458,953 | B2 | 12/2008 | Peyman |
| 9,707,128 | B2 * | 7/2017 | Rynerson ............ A61F 9/00781 |
| 2007/0293872 | A1 | 12/2007 | Peyman |
| 2008/0228127 | A1 | 9/2008 | Burns et al. |
| 2009/0182421 | A1 | 7/2009 | Silvestrini et al. |
| 2010/0004499 | A1 | 1/2010 | Brigatti et al. |
| 2012/0089072 | A1 | 4/2012 | Cunningham, Jr. |

(Continued)

OTHER PUBLICATIONS

State Intellectual Property Office of the People's Republic of China, Second Office Action issued in corresponding Chinese Application No. 20130312843.0, English Translation only, dated Oct. 9, 2017 (3 pages).

(Continued)

*Primary Examiner* — Benjamin J Klein
(74) *Attorney, Agent, or Firm* — Wood Herron & Evans LLP (57) ABSTRACT

A method and shunt device for treating glaucoma includes positioning a first end portion of a tube body into the retrobulbar space of an eye. The method also includes positioning a second end portion of the tube body into the anterior chamber of the eye. The tube body provides fluid passage for aqueous humor such that the aqueous humor flows from the first end portion into the retrobulbar space. A surgical kit for reducing the intraocular pressure in the eye includes the shunt device, an introducer, and a stylet. The introducer has a distal end for positioning in the retrobulbar space and a proximal end for positioning exterior of the eye. The introducer has a radius of curvature adapted to circumvent the eye for insertion into the retrobulbar space.

6 Claims, 8 Drawing Sheets

(56) References Cited

U.S. PATENT DOCUMENTS

2014/0148752 A1    5/2014    Litvin

OTHER PUBLICATIONS

State Intellectual Property Office of the People's Republic of China, First Office Action issued in corresponding Chinese Application No. 20130312843.0, English Translation only, dated Jan. 24, 2017 (9 pages).

European Patent Office, Search Report issued in corresponding European Patent Application No. EP14756737 dated Sep. 26, 2016, 6 pp.

European Patent Office, Extended European Search Report issued in corresponding EP Application No. 14756737.4, dated Jan. 17, 2017 (9 pages).

International Searching Authority, PCT Receiving Office, USPTO, International Search Report and Written Opinion issued in corresponding PCT Application No. PCT/US2014/016471, dated May 6, 2015 (13 pages).

* cited by examiner

METHOD AND APPARATUS FOR REDUCING INTRAOCULAR PRESSURE OF AN EYE

TECHNICAL FIELD

The present invention relates generally to a method and apparatus for reducing intraocular pressure of an eye and, more particularly, to treating glaucoma.

BACKGROUND

Aqueous humor is naturally produced within the posterior chamber of the eye and serves a beneficial role to the health and function of the eye itself. Most notably, the aqueous humor provides nutrition, such as amino acids and glucose, to various ocular tissues while simultaneously pressurizing the eye and maintaining the correct intraocular structure. For this reason, aqueous humor is continuously produced and drained from a healthy eye to provide these important nutrients and maintain proper intraocular pressure.

Normal intraocular pressure is generally between 10 mmHg and 20 mmHg. In order to maintain this pressure, aqueous humor inflows from the posterior chamber of the eye into the anterior chamber of the eye. Aqueous humor circulates throughout the anterior chamber where it nourishes the cornea, before exiting through the trabecular meshwork and into Schlemm's canal. From there, it flows into the surrounding lymphatic channels. Under normal, healthy conditions, this cycle of inflowing and outflowing aqueous humor continues unabated. However, in some instances, the drainage of the aqueous humor begins to slow due to an obstruction in the outflow from the eye. Because the inflow remains the same while the outflow decreases, intraocular pressure within the eye begins to increase over time. Generally, intraocular pressures over 20 mmHg are considered a higher risk for damaging the optic nerve, and may result in glaucomatous optic nerve loss. The effects of glaucoma are irreversible and, if left untreated, may lead to partial or complete blindness. In the United States alone, more than 120,000 people have been diagnosed as clinically blind as a direct result of the debilitating effects of glaucoma. In fact, about 10% of all blindness in the United States is caused by glaucoma. In the event glaucoma is detected in a patient, it is important to quickly and effectively reduce intraocular pressure within the eye in order to prevent further damage to the optic nerve and preserve the patient's remaining vision.

Various treatments for glaucoma have been developed, but with mixed results. Initially, glaucoma may be treated with medication in the form of eyedrops or pills to either decrease the inflow or increase the outflow of aqueous humor. If this treatment fails, surgery may be necessary to reduce intraocular pressure. This can involve laser procedures which treat the trabecular meshwork resulting in increased outflow, or treat the production site of aqueous humor, the ciliary body, resulting in reduced inflow. Other surgical procedures for treating glaucoma generally involve creating a drainage system within the eye for directing aqueous humor from the anterior chamber to another location within or around the eye to be reabsorbed by the lymphatic system. Frequently, a surgeon directs the aqueous humor to a bleb formed with the conjunctiva tissue under the conjunctiva itself. This fluid connection to the bleb creates a sealed system in which the aqueous humor travels. Unfortunately, the healing characteristics of the eye work against the formation and maintenance of the bleb. As such, blebs are prone to scar down to the conjunctiva and/or become encapsulated, effectively blocking the outflow of the aqueous humor and, once again, increasing intraocular pressure.

In order to reduce the likelihood of bleb failure, plates may be placed on top of the sclera and sewn against the sclera in order to create additional space to maintain the bleb. Generally, the additional space creates a larger bleb, thus reducing the likelihood of the bleb scaring down. While this has proven mildly successful, the system must be sewn absolutely watertight or the bleb will still leak, scar down, and fail. Such watertight seals are often times difficult to form and extremely time consuming to create. Similarly, the fluid connection to the anterior chamber also is at risk for scaring closed or completely plugging with adjacent iris tissue. To some extent, valve implants may also be used to maintain these fluid connections and facilitate the outflow of aqueous humor. Unfortunately, for many patients, these too can become surrounded by tough fibrous inflammatory tissues, called encapsulation, rendering the entire procedure ineffective.

Moreover, these leaks, bleb failures, and fluid connections are difficult to detect in the time immediately following the surgery. For this reason, repeated follow-up visits to the surgeon are required. Should the bleb fail over time, the patient has few, if any options to repair the bleb. Typically, the patient must undergo another time consuming, complex, tedious surgery hoping to create a new bleb prone to the same, inherent risks of failure.

There is a need for a method and device for reducing intraocular pressure, particularly in the treatment of glaucoma, that addresses present challenges and characteristics such as those discussed above.

SUMMARY

In one embodiment of the invention, a method of reducing intraocular pressure of an eye with a shunt device includes positioning a first end portion of a tube body into a retrobulbar space of an eye. The method also comprises positioning a second end portion of the tube body into an anterior chamber of the eye. Thereby, the tube body provides fluid passage for aqueous humor from the anterior chamber of the eye to the retrobulbar space, whereby the aqueous humor flows from the first end portion into the retrobulbar space.

In one aspect, the method also includes maintaining a space between the first end portion and a retro-orbital tissue with a stent basket. The stent basket is coupled to the first end portion so that aqueous humor passes through the stent basket and into the retrobulbar space. In another aspect, implanting the shunt device positions a portion of the tube body between a sclera and a conjunctiva of the eye.

In another embodiment of the invention, a shunt device for reducing intraocular pressure within the anterior chamber of an eye comprises a tube body and a stent basket. The tube body has a first end portion and a second end portion and is flexible with a lumen extending therethrough. The first end portion has an outlet adapted for being positioned within a retrobulbar space of the eye. The second end portion has an inlet adapted for being positioned within the anterior chamber of the eye. The stent basket is coupled to the first end portion of the tube body and is in fluid communication with the outlet. Furthermore, the tube body is configured to allow pressurized aqueous humor to flow from within the anterior chamber to the retrobulbar space.

In one aspect, the shunt device also has a stent basket with a first stent end and a second stent end. The first stent end is closed, and the second stent end is coupled to the first end portion of the tube. In addition, the first and second stent ends are tapered for improving the insertion and removal of the stent basket from an introducer inserted into the eye.

In yet another embodiment of the invention, a surgical kit for reducing intraocular pressure within the anterior chamber of an eye comprises a shunt device, an introducer, and a stylet. The shunt device is flexible and includes a tube body having a first end portion, a second end portion, and a lumen therethrough. The introducer has a distal end and a proximal end and is generally rigid with a cavity extending therethrough. The cavity is sized to receive the tube body. Furthermore, the introducer has a length and a radius of curvature configured to circumvent the eye for accessing the retrobulbar space with the distal end. The introducer is also adapted to be removed proximally from the tube body such that only the first end portion of the tube body remains in the retrobulbar space. The stylet has a handle and a piercing end. The stylet is sized to insert into the proximal end of the introducer such that the piercing end extends distally from the distal end of the introducer. The piercing end is configured to pierce tissue surrounding the eye for positioning the distal end of the introducer in the retrobulbar space.

In one aspect, the introducer has an outer diameter, an inner diameter, and a radius of curvature. The outer diameter is from about 2 millimeters to about 3 millimeters, the inner diameter is from about 1.5 millimeters to about 2.5 millimeters, and the radius of curvature is from about 3 inches to about 4 inches.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
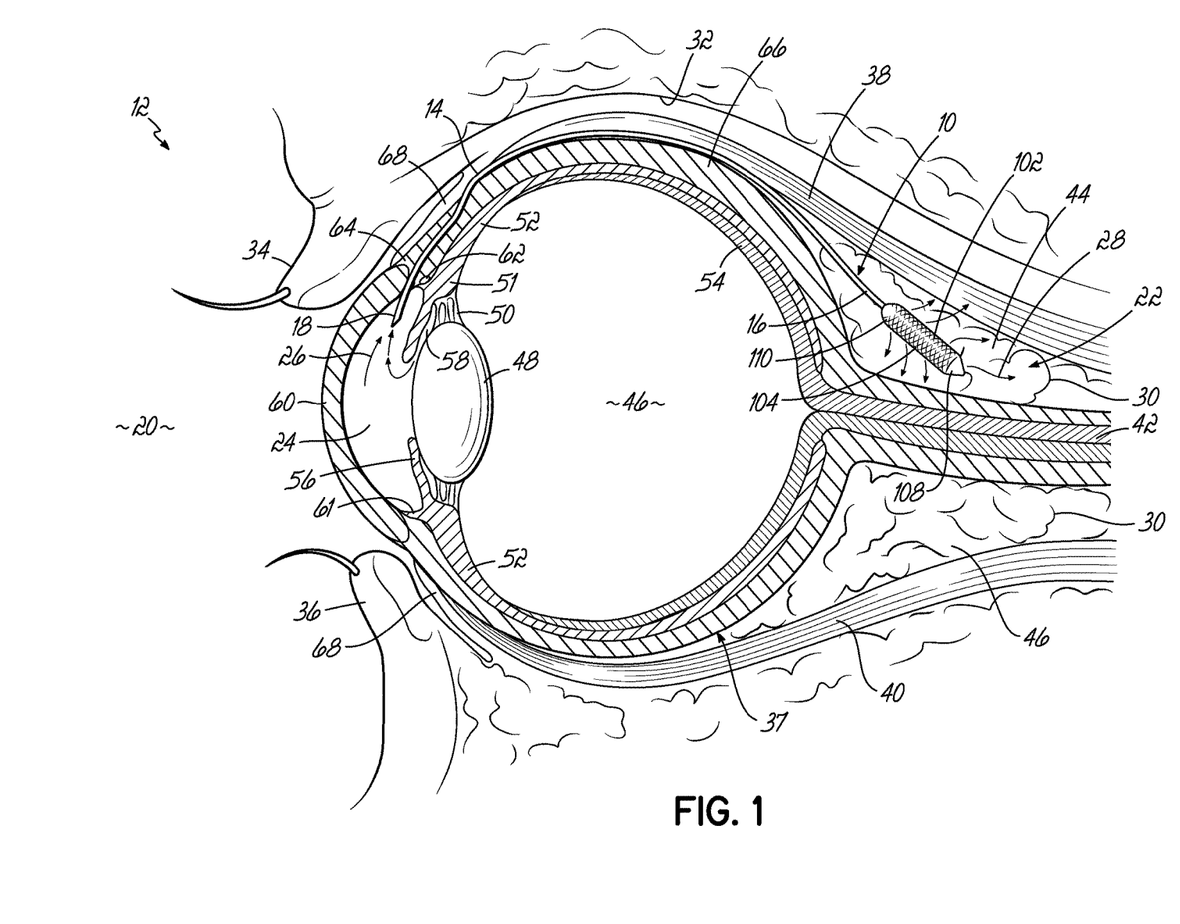
FIG. 1 is a cross-sectional view of an eye having a shunt device for treating glaucoma implanted therein.

With reference to FIG. 1, an embodiment of a shunt device 10 for reducing intraocular pressure is shown as implanted within an eye 12. The shunt device 10 generally comprises a tube body 14 having a first end portion 16 and a second end portion 18. The shunt device 10 is implanted within the eye 12 during a surgical procedure described below in additional detail. With reference to directions relative to the eye 12 shown in FIG. 1, an exterior 20 is proximal to the eye 12 while a retrobulbar space 22 is distal of the eye 12. The surgical procedure is performed by a surgeon, such as a trained ophthalmologist or similarly qualified professional, in order to fluidly connect an anterior chamber 24 of the eye 12 to the retrobulbar space 22.

Accordingly, the tube body 14 is adapted to provide fluid passage for aqueous humor from the anterior chamber 24 to the retrobulbar space 22 for reducing elevated intraocular pressure to normal, or otherwise healthy, intraocular pressure. For instance, aqueous humor flows from the anterior chamber 24 to the retrobulbar space 22 with a flow rate sufficient to maintain intraocular pressure generally between 10 mmHg and 20 mmHg. With respect to FIG. 1, an inflow of the aqueous humor from the anterior chamber 24 is indicated by arrows 26, and an outflow of the aqueous humor into the retrobulbar space 22 is indicated by arrows 28. The retrobulbar space 22 includes retro-orbital tissue 30 known to absorb approximately 5 cc to 6 cc of an anesthetic, such as lidocaine or MARCAINE®, used in retrobulbar blocks. In this same way, the retrobulbar space 22 will be used to absorb aqueous humor, effectively draining the anterior chamber 24 of excess aqueous humor for reducing the intraocular pressure therein.

The schematic cross-section of the eye 12 will further aid in the understanding of the invention described herein. Generally, the eye 12 is positioned within an eye socket 32. An upper eyelid 34 and a lower eyelid 36 are proximally positioned in the eye 12 and adjacent to the exterior 20. From a globe 37 of the eye 12, four primary extraocular muscles extend distally to the bony apex of the orbit, providing a general boundary for a cone-shaped retrobulbar space 22, which itself is distally positioned within the eye 12, behind the globe 37 and within the extraocular muscles. More particularly, a superior rectus extraocular muscle 38 extends along the top of the globe 37 and transits the retrobulbar space 22, while an inferior rectus extraocular muscle 40 extends along the bottom of the eye 12 and transits the retrobulbar space. Similarly, the retrobulbar space 22 is transmitted centrally by an optic nerve 42 extending rearwardly from the globe 37. First, a superotemporal quadrant 44 of the retrobulbar space 22 is generally superior and lateral to the optic nerve 42, and below and lateral to the superior rectus muscle 38. Second, an inferotemporal quadrant 46 of the retrobulbar space 22 is generally inferior and lateral to the optic nerve 42, and superior and lateral to the inferior rectus muscle 40. Both the superotemperal quadrant 44 and the inferotemporal quadrant 46 of the retrobulbar space 22 generally comprise a lateral space of retro-orbital tissue 30 that, due to its high fat content, high vascularity, and high lymphatics content, is extremely absorptive of any fluids that transudate from existing vessels or lymphatics, or of any fluids placed into the retrobulbar space.

A central portion of the eye 12 is a vitreous cavity 46 positioned proximal of the optic nerve 42. A crystalline lens 48 is positioned proximal of the vitreous cavity 46 and supported by surrounding suspensory ligaments 50, i.e., zonules, connected to a ciliary body 51 which is responsible for the aqueous production within the eye 12. The ciliary body 51 is contiguous with the highly vascular choroid layer 52, which supplies oxygenation and nourishment to the outer layer of a retina 54 and forms an innermost layer of the eye 12 and serves to convert light into electrical signals that may be transferred along the optic nerve 42.

Furthermore, an annular iris 56 is positioned proximal of the lens 48. Generally, the iris 56 functions to modulate the amount of light entering the eye 12. However, the iris 56 also splits a proximal portion of the eye 12 into two chambers. A posterior chamber 58 is positioned between the iris 56 and the lens 48. Aqueous humor is formed within the posterior chamber 58 by the ciliary body 51 and inflows around the inner margin of the iris 56 and into the anterior chamber 24 that is positioned directly proximal from the iris 56. The anterior chamber 24 is proximally bounded by a domed, clear cornea 60. In this way, the anterior chamber 24 is generally defined by the space between the cornea 60 and the iris 56, while the posterior chamber 58 is generally defined by the space between the iris 56 and the lens 48.

In the event that the eye 12 is healthy, the aqueous humor flows out of the anterior chamber 24 through a ring of fenestrated tissue located at the junction of the base of the cornea and the root of the iris known as a trabecular meshwork 61. The aqueous humor then enters a collecting channel known as the Canal of Schlemm 62. The canal of Schlemm 62 is positioned in a ring, inwardly adjacent to an annular junction known as a limbus 64 and just external to the trabecular meshwork 61. The limbus 64, generally, is a junction of a generally spheroidal sclera 66 and the domed cornea 60. The sclera 66 generally serves to support and shape the eye 12 and acts as an outer layer, relative to the choroid 52, that protects the inner structures of the eye 12 discussed above. Further protection is provided to the eye 12 by a conjunctiva 68. The conjunctiva 68 is a thin membrane covering the proximal portion of the eye 12 and extends from the limbus 64, covers the sclera 66, and then returns back along the inside of the upper and lower eyelids 34, 36. Finally, collecting channels (not shown) from the canal of Schlemm 62 generally extend into the sclera 66 and connect with the lymphatics (not shown) of the globe 37. In this way, the aqueous humor may drain distally from the anterior chamber 24, into the lymphatic system (not shown), and enter into the blood stream (not shown).

Figure 2A:
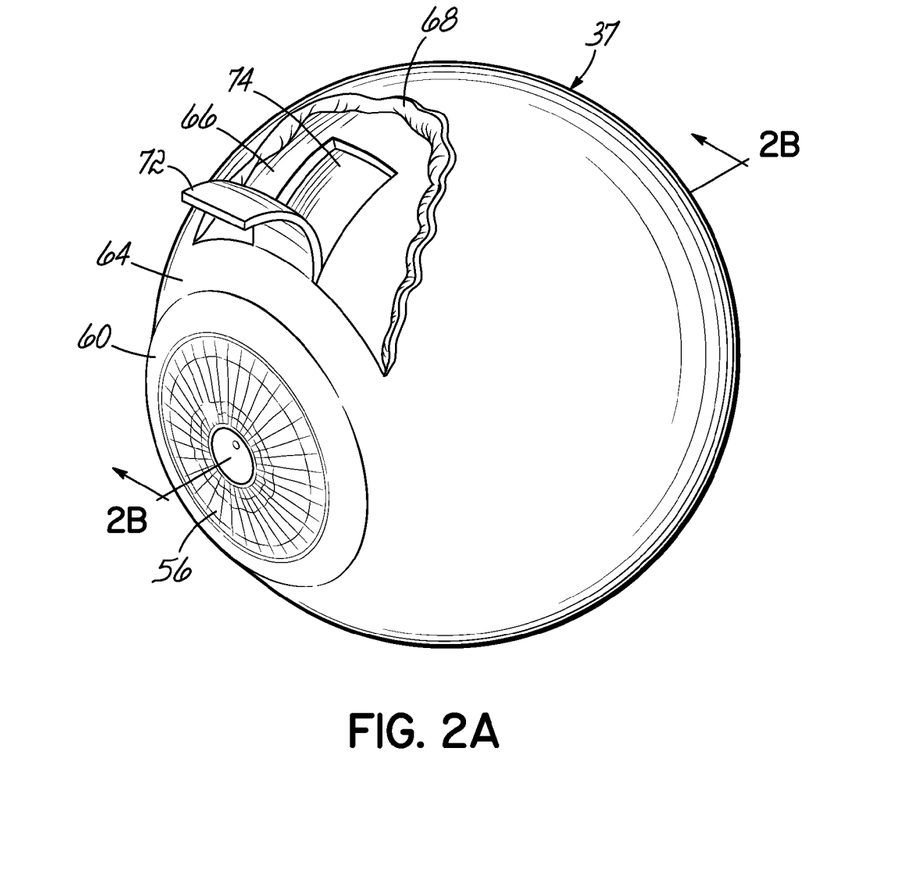
FIG. 2A is a perspective view of the eye of FIG. 1.
Figure 2B:
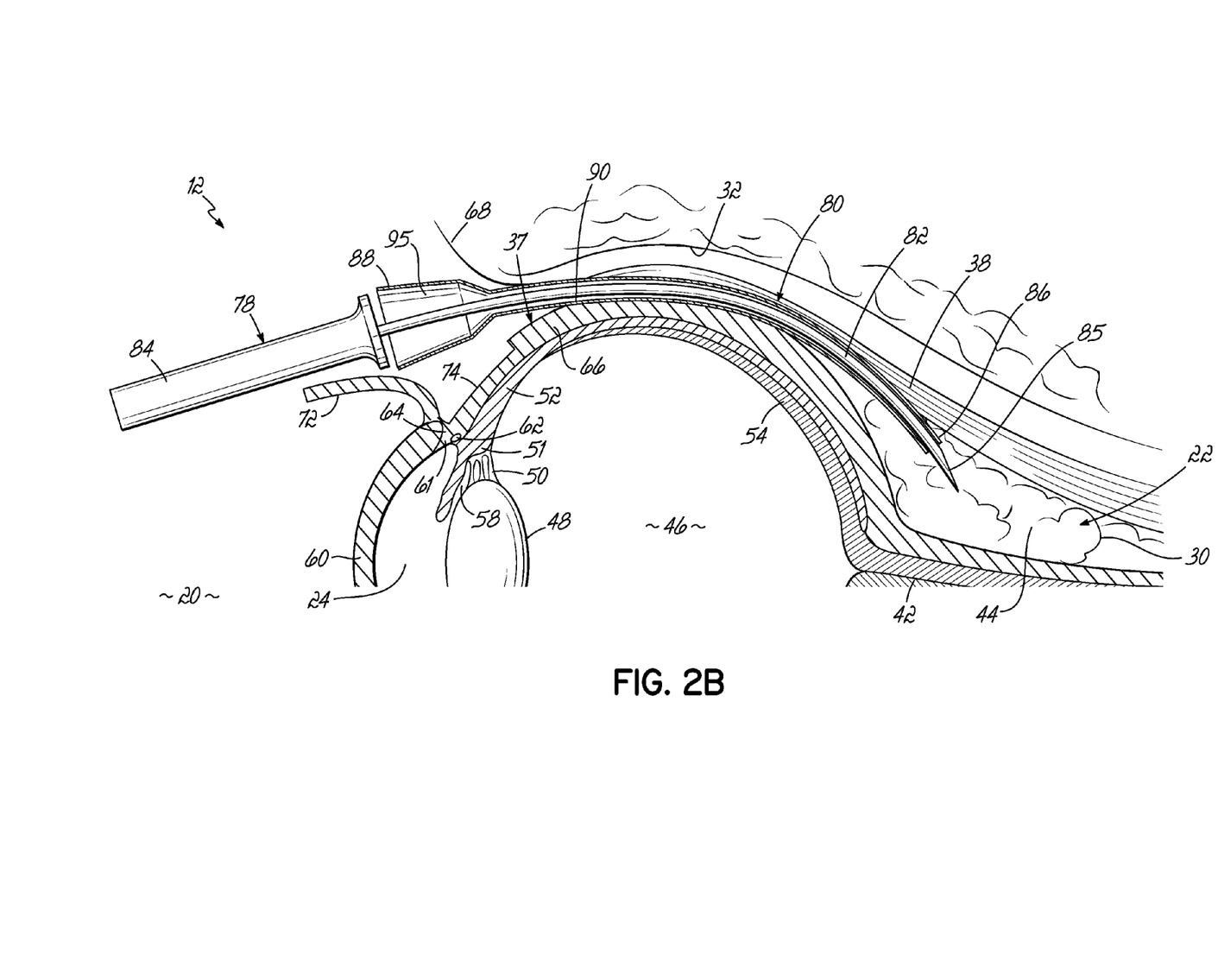
FIG. 2B is a cross-sectional view of a globe of the eye of FIG. 1 having an introducer inserted within the eye.

The method of implanting the shunt device 10 in the eye 12 begins as a peritomy procedure in order to facilitate eventual access to the anterior chamber 24 and sclera 66. FIG. 2A shows the globe 37 of the eye 12. An incision is made through the conjunctiva 68 adjacent to the limbus 64 and the cornea 60 with scissors (not shown). Accordingly, the conjunctiva 68 is resected and pulled back, as shown in FIG. 2A, in order to expose the sclera 66. Another incision is made at the exposed sclera 66 with a guarded step-knife (not shown) in order to make a mid-thickness sclera incision. Furthermore, a crescent blade (not shown) is used to dissect into the mid-thickness sclera incision and extended proximally to create a mid-thickness scleral flap 72 until the sclera flap 72 effectively folds proximally from the globe 37, and exposes the residual scleral bed 74 below, and the gray-line (not shown) at the proximal extent of the incision. The gray-line is the anatomic landmark for the point of eventual entry into the anterior chamber 24 through the trabecular meshwork 61. With respect to FIG. 2B, the sclera flap 72 is sized and drawn proximal from the globe 37 far enough to provide access through the gray-line (not shown) and into the anterior chamber 24 positioned proximal to the gray-line. The sclera flap 72 is then laid down against the residual scleral bed 74, while the remaining surgical steps are performed.

In order to access the retrobulbar space 22, the surgeon uses a surgical kit that includes a stylet 78 in conjunction with an arcuate introducer 80 and the shunt device 10 (see FIG. 1). The stylet 78 comprises a projecting member 82 coupled to a handle 84. The projecting member 82 is generally flexible and includes a sharp, piercing end 85 distal of the handle 84. The introducer 80 comprises a distal end 86, a proximal end 88, and a cavity 90 that extends therethough. The introducer 80 is generally rigid and shaped to extend from the exterior 20 of the eye 12 to the retrobulbar space 22. In addition, the introducer 80 is configured to circumvent the globe 37 while extending from the exterior 20 to the retrobulbar space 22. More particularly, the introducer 80 has a length and radius of curvature adapted to circumvent the globe 37 and extend into the retrobulbar space 22. For example, the introducer has a radius of curvature from about 3 inches to about 4 inches and a length of at least 1.25 inches or from about 1.25 inches to about 1.5 inches. More particularly, the introducer 80 has a radius of curvature of about 3 inches, a length of about 1.5 inches, and an outer diameter from about 2 millimeters to about 3 millimeters.

The distal end 86 is pointed for easing insertion of the introducer 80 into the retrobulbar space 22. In addition, the proximal end 88 of the introducer 80 is in the form of a funnel portion 95 that tapers distally toward the cavity 90 therein. The proximal end 88 receives the projecting member 82, which is configured to slide into the cavity 90 of the introducer 80. The projecting member 82 is also of sufficient length such that the piercing end 85 extends distally from the distal end 86 while the handle 84 extends proximally from the introducer 80. Thereby, the surgeon may grip and manipulate the movement of the introducer 80 and stylet 78 simultaneously at the interface of the handle 84 and funnel portion 95, while inserting the introducer 80 into the eye 12 with the piercing end 85 extending therefrom.

The piercing end 85 pierces tissue surrounding the eye 12 in order to position the distal end 86 of the introducer 80 in the retrobulbar space 22. More particularly, the piercing end 85 and introducer 80 are inserted above the eye 12 in order to position the introducer 80 within the cone of the extraocular muscles extending distally from the globe 37 and, more specifically, within in the superotemporal quadrant 44 of the retrobulbar space 22. However, it will be appreciated that other quadrants of the retrobulbar space 22, such as the infertemporal quadrant 46, may also be used in the procedure as described herein. Of course, in the event of accessing another quadrant of the retrobulbar space 22, the peritomy described above will need to be positioned elsewhere respective to the chosen quadrant. In any case, the introducer 80 is inserted into the eye 12 between the conjunctiva 68 and the sclera 66 and forced distally around the eye 12 in an arcuate path against the sclera 66. The distal end 86 continues distally into the superotemporal quadrant 44 of the retrobulbar space 22 until positioned about 0.25 inches distal of the globe 37. Once the introducer 80 is positioned as such, the stylet 78 is withdrawn from the introducer 80; thereby, giving the surgeon access the retrobulbar space 22 for implanting the shunt device 10 shown in FIG. 2C.

Figure 2C:
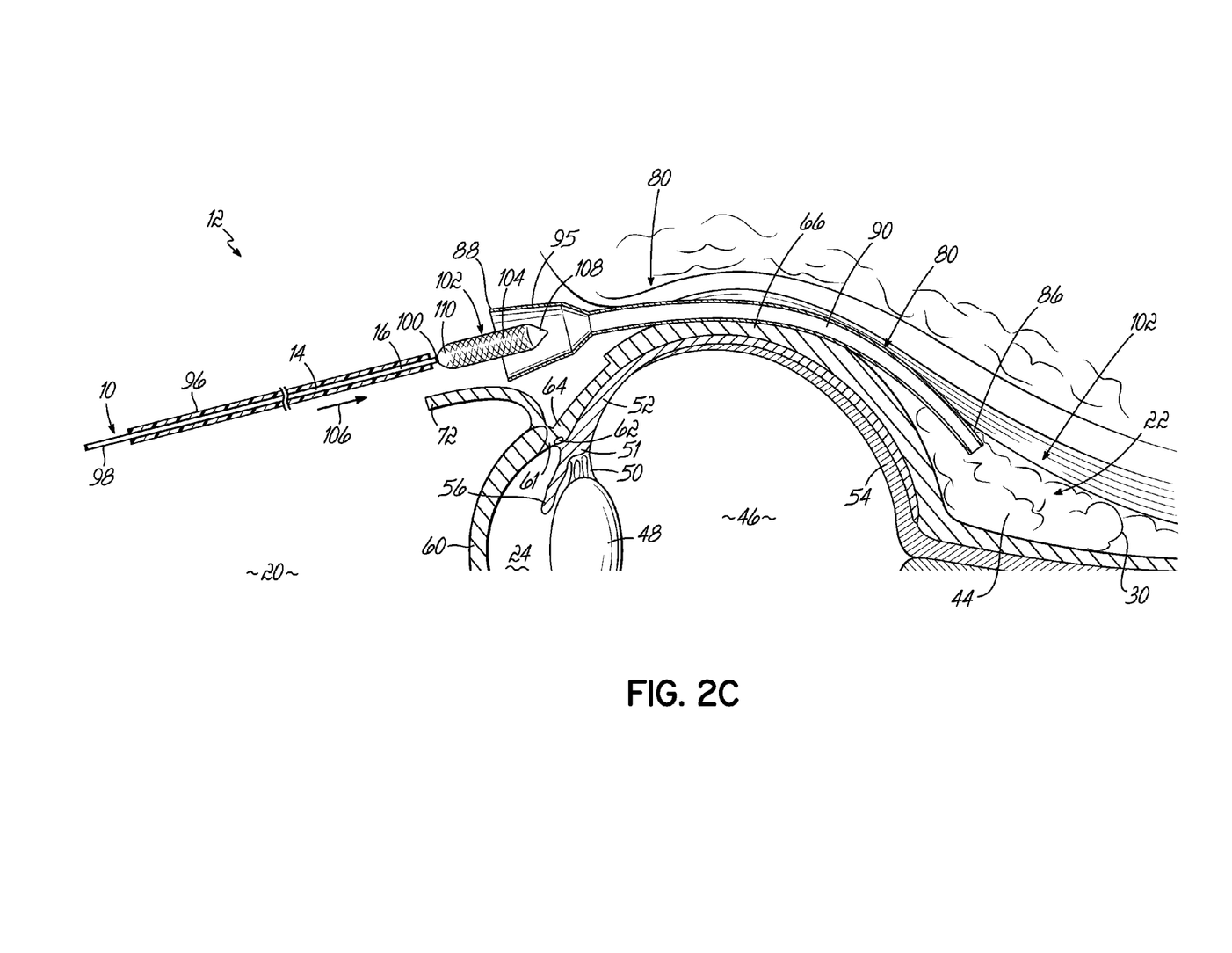
FIG. 2C is the cross-sectional view of the eye of FIG. 2B and the shunt device being inserted into the eye.

With respect to FIG. 2C, a sleeve 96 is slidably positioned over the tube body 14 to aid in sliding the tube body 14 along the cavity 90 within the introducer 80. The cavity 90 has an inner diameter adapted to receive the tube body 14. More particularly, the inner diameter of the cavity 90 is from about 1.5 to about 2.5 millimeters. The sleeve 96 is semi-rigid and supports the tube body 14 to prevent the tube body 14 from damage, such as deformation, that may occur while implanting the shunt device 10. More particularly, the sleeve 96 has an inner diameter from about 0.6 millimeters to about 0.8 millimeters and an external diameter from about 1.1 millimeters to about 1.4 millimeters. More particularly, the inner diameter is about 0.7 millimeters, and the external diameter is about 1.25 millimeters. The tube body 14 is a silicon transfer tubing manufactured from flexible medical grade silicon configured to be implanted in the body. The tube body 14 defines a lumen 98. The lumen 98 has an outlet 100 at the first end portion 16. The lumen 98 has a diameter from about 0.2 millimeters to about 0.4 millimeters, and the tube body has an outer diameter from about 0.55 millimeters to about 0.75 millimeters with a length of about 4 inches. More particularly, the lumen 98 has a diameter of about 0.3 millimeters, and the tube body has an outer diameter of about 0.65 millimeters. The flow rate of aqueous humor through lumen 98 may be chosen by selecting the diameter of the lumen 98 that produces a desired flow rate. In addition, a medical grade stent basket 102 is coupled to the first end portion 16 and, as shown, is formed onto the first end portion 16 of the tube body 14. The stent basket 102 is in the form of a mesh structure 104 with an internal void space defined by the mesh structure 104. More particularly, the stent basket 102 is from about 5 millimeters to about 8 millimeters in length, depending on the amount of pressure reduction needed. More particularly, the stent basket 102 is generally from about 2 millimeters to about 3 millimeters in diameter. The mesh structure 104 is collapsible when forced into the funnel portion 95 of the introducer 80 and re-opens when exiting the distal end 86 of the introducer 80. According to the exemplary embodiment, the void space of the stent basket 102 is about 0.02 cubic centimeters. As such, the stent basket 102 is adapted to allow aqueous humor to pass through the void space while the mesh structure 104 maintains a space between the outlet 100 and the retro-orbital tissue 30.

Figure 2D:
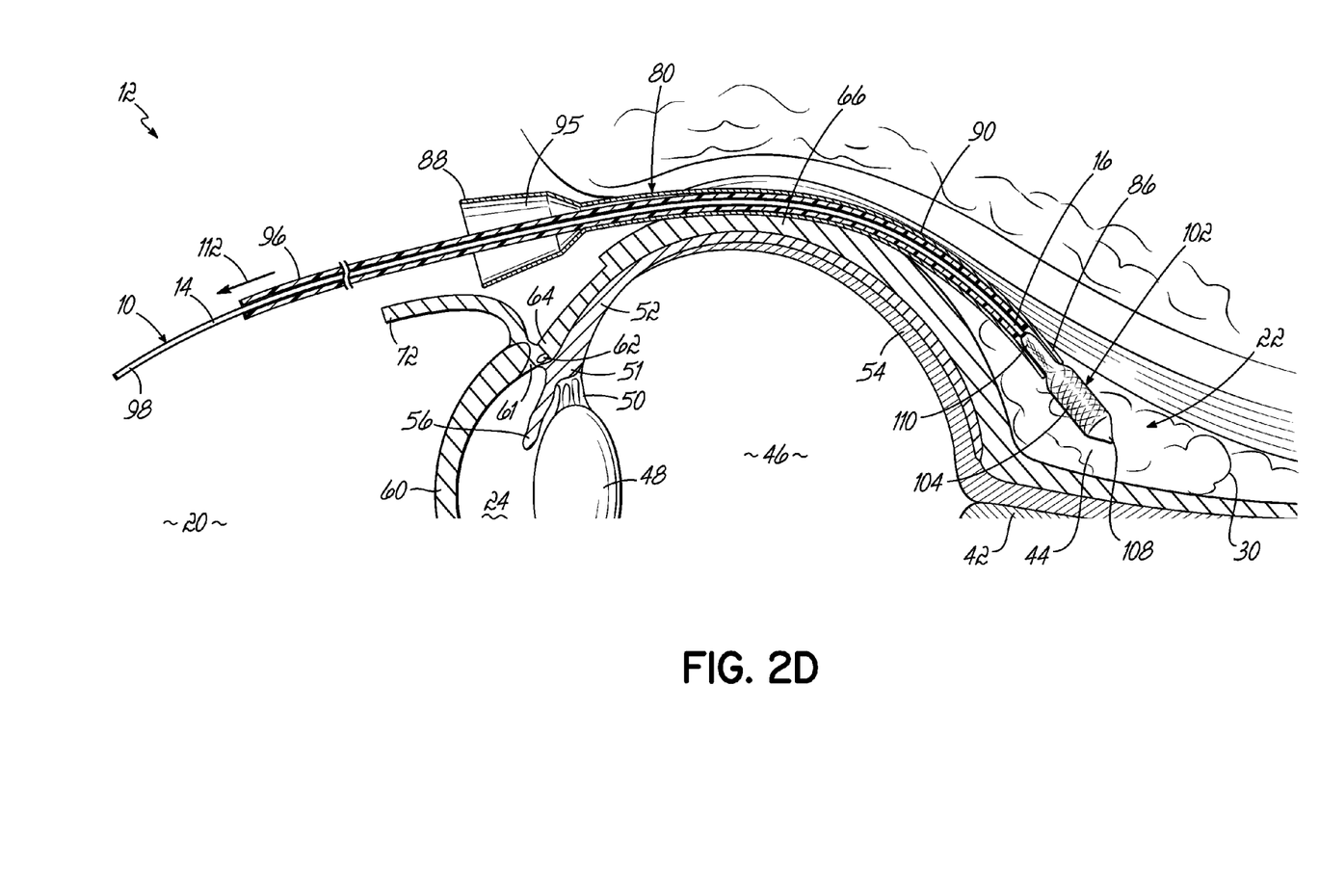
FIG. 2D is the cross-sectional view of the eye of FIG. 2C and a sleeve of the shunt device being removed from the eye.

With respect to FIGS. 2C and 2D, the surgeon inserts the tube body 14 and the stent basket 102 into the introducer 80, as indicated by arrow 106. More particularly, the first end portion 16 is positioned generally 0.25 inches behind the globe 37, as described above. In order to insert the stent basket 102, the mesh structure 104 is collapsible from an expanded configuration to a contracted configuration when sufficient force is applied to the mesh structure 104. This force is applied when the stent basket 102 is forced within the cavity 90. However, in order to aid in collapsing the mesh structure 104, a first stent end 108 and a second stent end 110 are tapered. The second stent end 110 is formed onto the first end portion 16 of the tube body 14 open to the outlet 100. In contrast, the first stent end 108 is formed of the mesh structure 104 and relatively closed, except for the void space within the mesh structure. The tapered first and second stent ends 108, 110 help to funnel and contract the mesh structure 104 as the mesh structure 104 moves in and/or out of the tube body 14. In this way, the stent basket 102 may be implanted or removed from the retrobulbar space 22 by way of the tube body 14 used in conjunction with the introducer, without damaging the eye 12. According to the exemplary embodiment, the stent basket 102 has an expanded diameter from about 2 millimeters to about 3 millimeters in the expanded configuration and a contracted diameter of from about 1.5 millimeters to about 2.5 millimeters in the contracted configuration. While the exemplary embodiment shows the stent basket 102, it will be appreciated that the invention described herein is not intended to be limited as such. More particularly, the stent basket 102 may also be deployed from the contracted configuration to the expanded configuration using any device and/or method known to one of ordinary skill. For example, the stent basket 102 may be deployed using an additional expansion device (not shown), such as a dilation balloon. One such a device and method is described in U.S. Pat. No. 6,019,777, the disclosure of which is hereby incorporated by reference herein. In the alternative, the shunt device 10 may not include a stent basket 102.

Figure 2E:
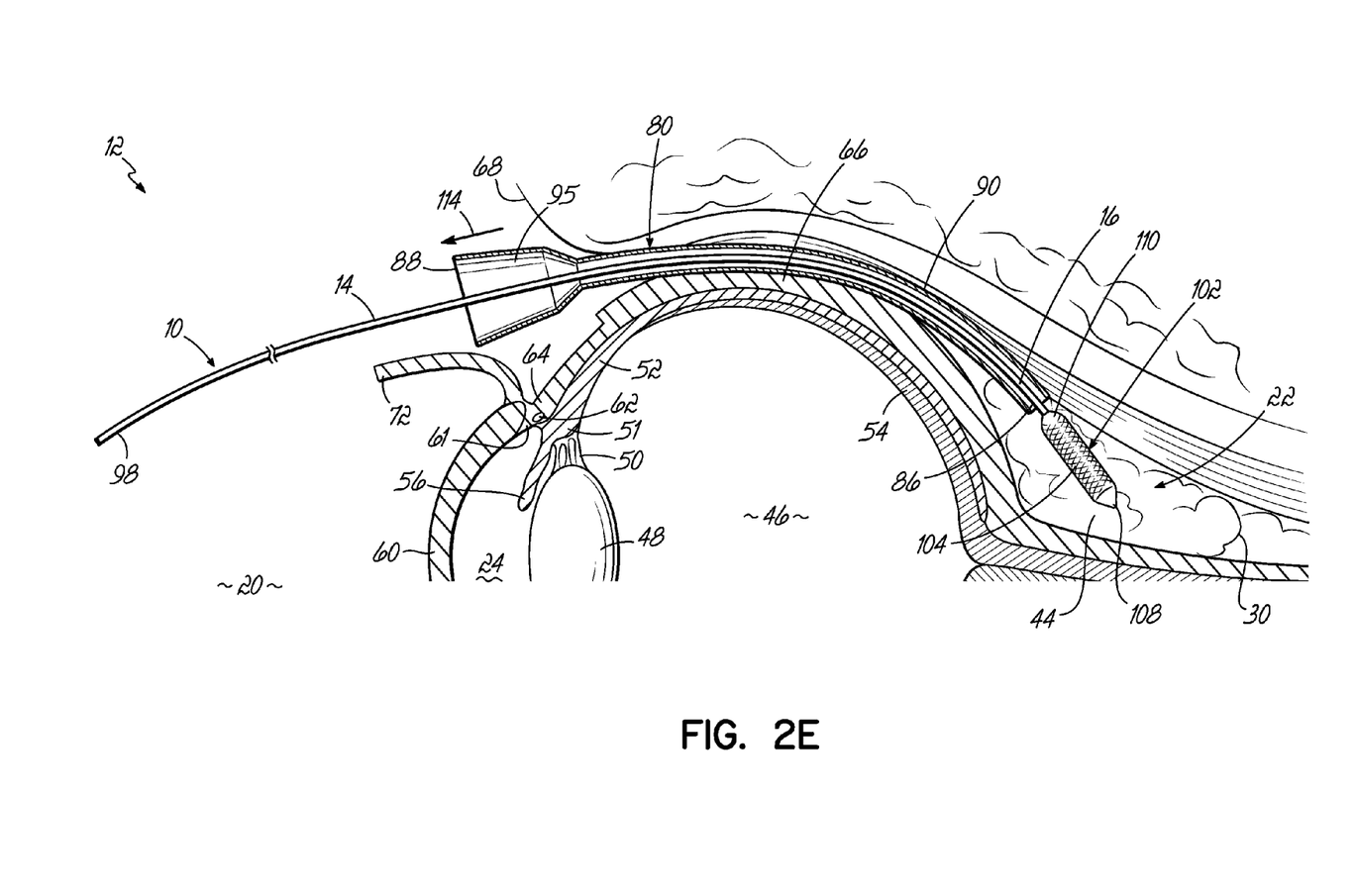
FIG. 2E is the cross-sectional view of the eye of FIG. 2D and the introducer being removed from the eye.

Once the first end portion 16 is implanted or otherwise positioned within the retrobulbar space 22, the tube body 14 is held relatively stationary while the sleeve 96 is withdrawn from the introducer 80, as indicated by arrow 112 in FIG. 2D. Similarly, as shown in FIG. 2E, the introducer 80 is withdrawn from the retrobulbar space 22 along the same path with which it was inserted into the eye 12 as indicated by arrow 114. Thus, all that remains within the eye 12 is some portion of the tube body 14 positioned between the sclera 66 and conjunctiva 68 and the first end portion 16 in the retrobulbar space 22 shown in FIG. 2F.

Figure 2F:
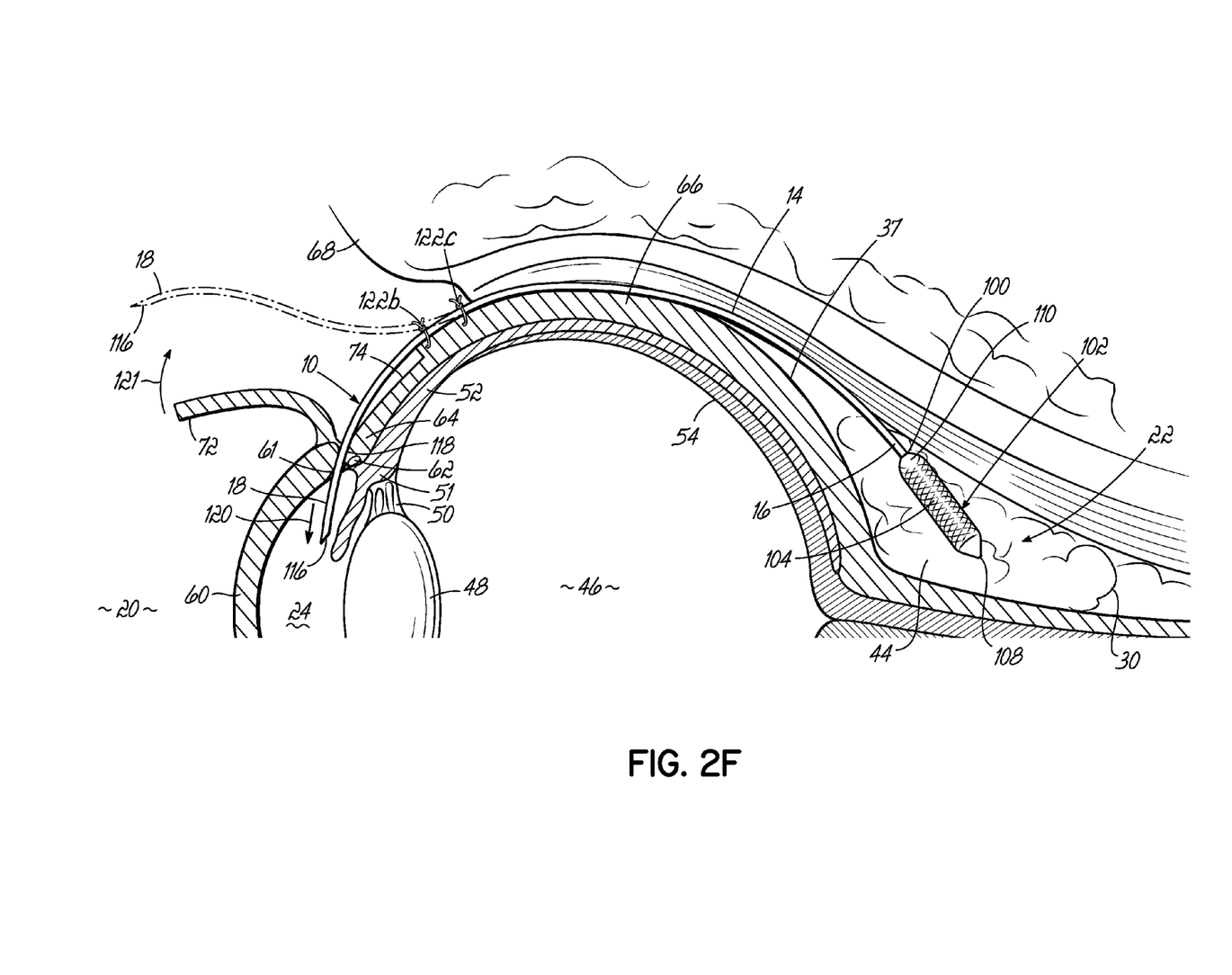
FIG. 2F is the cross-sectional view of the eye of FIG. 2E and the shunt device being positioned within the eye.

As mentioned briefly above, the tube body 14 is at least about 4 inches long in order to provide ample length with which to manipulate the tube body 14. However, FIG. 2F shows that the tube body 14 is cut, such as a bevel cut, to form the second end portion 18 of the tube body 14. Thereby, the lumen 98 has an inlet 116 at the second end portion 18. After forming the second end portion 18, the length of the shunt device 10 from the first end portion 16 to the second end portion 18 is about 1.25 inches. However, it will be appreciated that the length may be adapted to accommodate the distance from the retrobulbar space 22 to the anterior chamber 24 that may be relatively unique to each patient.

Figure 2G:
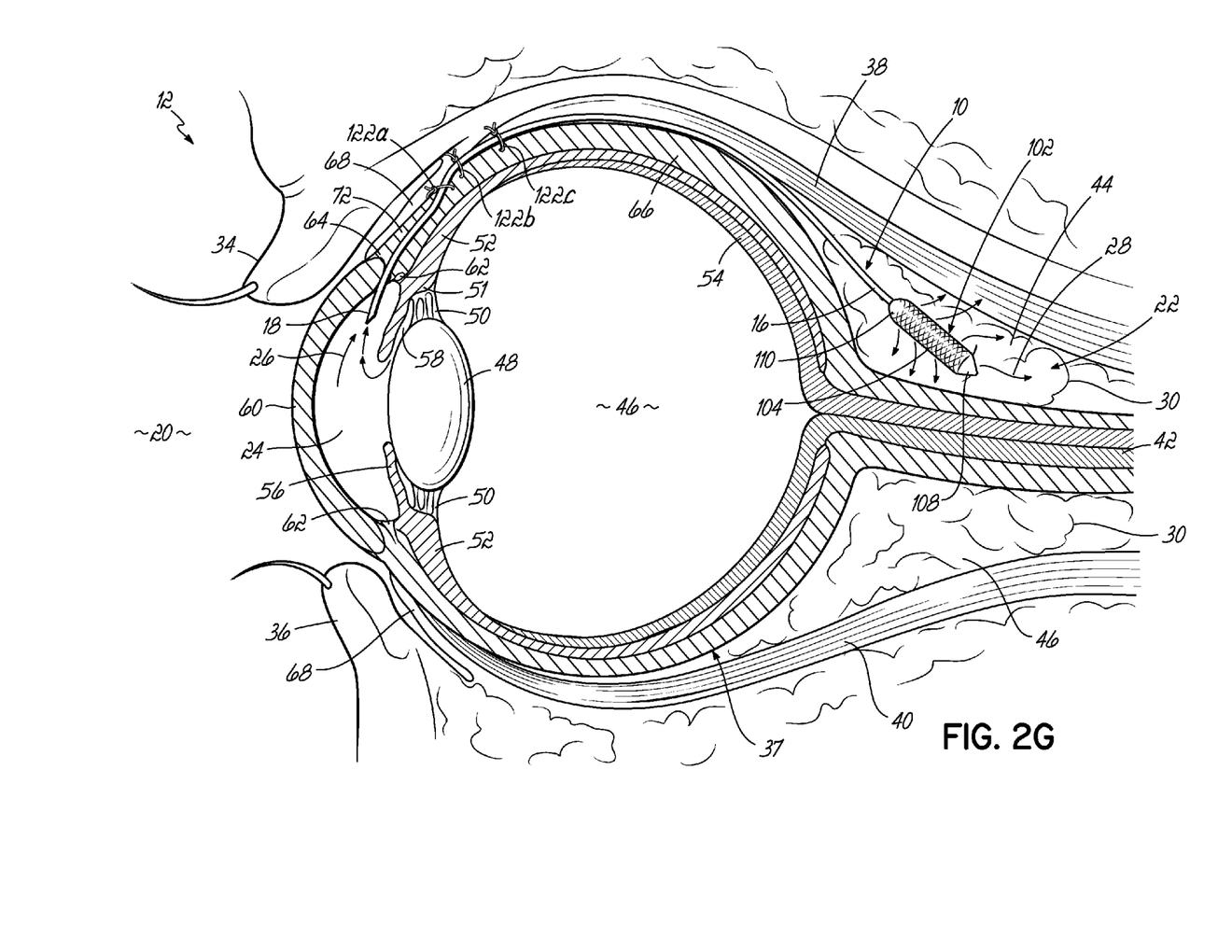
FIG. 2G is the cross-sectional view of the eye of FIG. 2F and the shunt device implanted within the eye.

A needle (not shown), such as a 27 gauge needle, is inserted through the gray line portion 74 and into the anterior chamber 24 in order to form an access hole 118 therethrough. Once the access hole 118 is formed, the second end portion 18 is inserted through the access hole 118 and into the anterior chamber 24 as indicated by arrow 120. More particularly, the second end portion 18 is inserted into the anterior chamber 24 from about 2 millimeters to about 4 millimeters. In addition, the tube body 14 is attached to the globe 37 and the sclera flap 72 is sewn back to the sclera 66 as shown in FIGS. 2F and 2G. More particularly, a plurality of sutures 122a, 122b, 122c are positioned around the tube body 14 and through the sclera 66 to attach the shunt device 10 to the globe 37. The sclera flap 72 is laid over the access hole 118 and the tube body 14, as indicated by arrow 121. At least one suture 122a is positioned through the sclera flap 72 and the sclera 66 in order to ensure proper healing of the sclera 66 at this incision location. However, two of the sutures 122a may also be used to sew down the sclera flap 72 if necessary. Additional sutures 122b, 122c may also be positioned through the sclera 66 distal of the sclera flap 72. On one hand, these additional sutures 122b, 122c help maintain the position of the tube body 14. On the other hand, the additional sutures 122b, 122c are tightened over the tube body 14 to constrict the lumen 98 therein. Accordingly, flow of aqueous humor from the inlet 116 to the outlet 100 may be restricted to selectively limit the flow of the aqueous humor from the anterior chamber 24. According to the exemplary embodiment, the plurality of sutures 122a, 122b, 122c are formed from nylon and placed about 1 centimeter apart. The sutures 122a, 122b, 122c, as shown in the exemplary embodiment, are 10-0 interrupted sutures; however, it will be appreciated that a long mattress suture (not shown) may also be used. In any case, with the first and second end portions 16, 18 appropriately positioned as described above and the tube body 14 sutured to the sclera 66, the shunt device 10 is now implanted within the eye 12 for fluidly communicating aqueous humor from the anterior chamber 24 to the retrobulbar space 22 as shown in FIG. 2G.

After approximately four to six weeks, the patient should return to the surgeon for a follow-up appointment to ensure that the shunt device 10 is functioning as intended. In the event that the surgeon chooses to increase the flow rate of the aqueous humor to the retrobulbar space 22, the surgeon may selectively tighten or release one or more of the sutures 122a, 122b, 122c in order to respectively decrease or increase the diameter of the lumen 98. Thereby, the flow rate of the aqueous humor may be selectively decreased or increased by restricting or expanding the tube body 14. However, once the flow rate of the aqueous humor is selected by the surgeon and the shunt device 10 is functioning properly, the patient does not need to return for follow-up appointments related specifically to the implanted shunt device 10. On one hand, previous glaucoma treatments using blebs require regular follow-up appointments, because the risk of the bleb to scaring down is continuous. On the other hand, the shunt device 10, described above, works in conjunction with the natural ability of the eye 12 to heal and scar down. Moreover, there is no need for a watertight conjunctival closure since the aqueous humor is being directed into the retrobulbar space 22, which is relatively naturally-sealed. In this way, the implantation of the shunt device 10 is considerably simpler and less time consuming than previous treatments.

In the event that the shunt device 10 requires removal from the patient's eye 12, the above treatment need only be practiced generally in reverse. More particularly, the plurality of sutures 122a, 122b, and 122c should be released and the second end portion 18 should be removed from the anterior chamber 24. The introducer 80 is slid over the tube body 14 and inserted into the eye 12 along the same path described above. With the introducer 80 once again positioned in the retrobulbar space 22, the tube body 14 is withdrawn through the introducer 80. Accordingly, the tapered second stent end 110 forced against the introducer 80 contracts the stent basket 102 and the entire shunt device 10 may be removed from the eye 12. Finally, the introducer 80 is similarly withdrawn from the eye 12 to complete the reversal of the method.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A surgical kit for reducing intraocular pressure within the anterior chamber of an eye, comprising;
a shunt device, a sleeve, an introducer, and a stylet;
the shunt device comprising a tube body having a first end portion and a second end portion, the tube body being flexible with a lumen extending therethrough, the first end portion having an outlet adapted for being positioned within a retrobulbar space of the eye, the second end portion having an inlet adapted for being positioned within an anterior chamber of the eye, the tube body being configured to be inserted into the sleeve and the introducer for guiding the first end portion of the tube body into the retrobulbar space;
the sleeve being positioned over the tube body to aid in the tube body in sliding within the introducer, the sleeve adapted to be removed proximally from the tube body and introducer;
the introducer having a distal end and a proximal end, the introducer being generally rigid and having a cavity extending therethrough sized to receive the tube body and the sleeve, the introducer having a length and a radius of curvature configured to circumvent the eye for accessing the retrobulbar space with the distal end, the introducer adapted to be removed proximally from the tube body such that only the first end portion of the tube body remains in the retrobulbar space; and
the stylet having a handle end and a piercing end, the stylet sized to insert into the proximal end of the introducer such that the piercing end extends distally from the distal end of the introducer, the piercing end configured to pierce tissue surrounding the eye for positioning the distal end of the introducer in the retrobulbar space.

2. The surgical kit of claim 1 further comprising a stent basket, the stent basket having a first stent end and a second stent end, the first stent end being closed and the second stent end coupled to the first end portion, wherein the first and second stent ends are tapered for guiding the stent basket into the introducer.

3. The surgical kit of claim 1 wherein the introducer has an outer diameter, the outer diameter being from about 2 millimeters to about 3 millimeters.

4. The surgical kit of claim 1 wherein the introducer has an inner diameter, the inner diameter being from about 1.5 millimeters to about 2.5 millimeters.

5. The surgical kit of claim 1 wherein the length of the introducer is at least about 1.25 inches for accessing the retrobulbar space.

6. The surgical kit of claim 1 wherein the radius of curvature of the introducer is from about 3 inches to about 4 inches.

* * * * *